United States Patent
Sie et al.

(10) Patent No.: US 8,551,045 B2
(45) Date of Patent: Oct. 8, 2013

(54) FLUID INFUSION SYSTEM, A METHOD OF ASSEMBLING SUCH SYSTEM AND DRUG RESERVOIR FOR USE IN THE SYSTEM

(75) Inventors: Gunnar Monrad Sie, Virum (DK); Carsten Lund, Vordingborg (DK); Niels Frederik Keiser-Nielsen, Niva (DK)

(73) Assignee: Novo Nordisk A/S, Basgvaerd (DK)

( * ) Notice: Subject to any disclaimer, the term of this patent is extended or adjusted under 35 U.S.C. 154(b) by 93 days.

(21) Appl. No.: 12/297,340

(22) PCT Filed: Apr. 19, 2007

(86) PCT No.: PCT/EP2007/053865
§ 371 (c)(1),
(2), (4) Date: Feb. 16, 2009

(87) PCT Pub. No.: WO2007/118907
PCT Pub. Date: Oct. 25, 2007

(65) Prior Publication Data
US 2009/0299288 A1    Dec. 3, 2009

Related U.S. Application Data

(60) Provisional application No. 60/797,447, filed on May 3, 2006.

(30) Foreign Application Priority Data

Apr. 19, 2006    (DK) ............................ PA 2006 00540

(51) Int. Cl.
*A61M 1/00*    (2006.01)

(52) U.S. Cl.
USPC ........................................................ 604/151

(58) Field of Classification Search
USPC ......... 604/110, 111, 232, 151, 218, 220–222, 604/228; 92/29, 193–195; 277/437, 467, 277/470, 608

See application file for complete search history.

(56) References Cited

U.S. PATENT DOCUMENTS

| 1,799,463 A | 4/1931 | Hein |
| 3,215,320 A | 11/1965 | Harold et al. |

(Continued)

FOREIGN PATENT DOCUMENTS

| CH | 265347 | 11/1949 |
| DE | 1292787 | 4/1969 |

(Continued)

OTHER PUBLICATIONS

English language, machine generated translation for DE1292787 published on Apr. 17, 1969.

(Continued)

*Primary Examiner* — Nicholas Lucchesi
*Assistant Examiner* — Jenna Zhang
(74) *Attorney, Agent, or Firm* — Wesley A. Nicolas; Marc A. Began; Reza Green (57) ABSTRACT

The present invention relates to methods and devices for providing a reduced risk of free flow from medical devices such as an infusion pump. A medicament containing reservoir is provided with a piston having a sealing portion formed by a material of a first stiffness. The piston further comprises a frictional enhancing member having one or more reservoir wall engaging portions and being at least partly made of a material having a stiffness greater than the first stiffness. By arranging the frictional enhancing member to exert a radially outwards directed force component against the cylindrical wall an increased friction is provided between the piston and the reservoir wall.

16 Claims, 4 Drawing Sheets

(56) References Cited

U.S. PATENT DOCUMENTS

| | | |
|---|---|---|
| 3,827,602 A | 8/1974 | Nicholls |
| 3,939,833 A | 2/1976 | Hansson et al. |
| 4,055,177 A | 10/1977 | Cohen |
| 4,331,146 A | 5/1982 | Brignola |
| 4,381,779 A | 5/1983 | Margulies |
| 4,493,703 A * | 1/1985 | Butterfield ............ 604/110 |
| 4,498,904 A | 2/1985 | Turner et al. |
| 4,568,335 A | 2/1986 | Updike et al. |
| 4,710,170 A | 12/1987 | Haber |
| 4,973,318 A | 11/1990 | Holm et al. |
| 4,979,943 A * | 12/1990 | Trenner ............ 604/110 |
| 5,085,638 A * | 2/1992 | Farbstein et al. ............ 604/110 |
| 5,094,148 A | 3/1992 | Haber et al. |
| 5,222,942 A | 6/1993 | Bader |
| 5,279,585 A | 1/1994 | Balkwill |
| 5,300,041 A | 4/1994 | Haber |
| 5,304,152 A | 4/1994 | Sams |
| 5,331,954 A | 7/1994 | Rex et al. |
| 5,353,691 A | 10/1994 | Haber et al. |
| 5,370,628 A | 12/1994 | Allison et al. |
| 5,411,488 A * | 5/1995 | Pagay et al. ............ 604/218 |
| 5,462,535 A | 10/1995 | Bonnichsen et al. |
| 5,496,285 A | 3/1996 | Schumacher et al. |
| 5,531,693 A | 7/1996 | Vounatsos |
| 5,591,131 A | 1/1997 | Chen |
| 5,620,423 A * | 4/1997 | Eykmann et al. ............ 604/219 |
| 5,626,566 A | 5/1997 | Petersen et al. |
| 5,688,252 A | 11/1997 | Matsuda et al. |
| 5,875,976 A | 3/1999 | Nelson et al. |
| 5,928,202 A | 7/1999 | Linnebjerg |
| 5,947,929 A * | 9/1999 | Trull ............ 604/152 |
| 6,004,297 A | 12/1999 | Steenfeldt-Jensen et al. |
| 6,004,300 A | 12/1999 | Butcher et al. |
| 6,080,136 A | 6/2000 | Trull et al. |
| 6,142,978 A | 11/2000 | Niedospial et al. |
| 6,206,859 B1 | 3/2001 | Niedospial, Jr. et al. |
| 6,221,046 B1 | 4/2001 | Burroughs et al. |
| 6,221,053 B1 | 4/2001 | Walters et al. |
| 6,447,487 B1 | 9/2002 | Cane' |
| 6,569,126 B1 | 5/2003 | Poulsen et al. |
| 6,800,071 B1 * | 10/2004 | McConnell et al. ............ 604/155 |
| 2003/0120219 A1 | 6/2003 | Nielsen et al. |
| 2006/0151545 A1 | 7/2006 | Imhof et al. |

FOREIGN PATENT DOCUMENTS

| | | |
|---|---|---|
| DE | 4423753 | 2/1996 |
| EP | 0204977 | 12/1986 |
| EP | 327910 | 8/1989 |
| EP | 497567 | 8/1992 |
| EP | 0395211 | 12/1994 |
| EP | 0893133 | 1/1999 |
| EP | 1002551 | 5/2000 |
| FR | 2003495 | 11/1969 |
| GB | 836279 | 6/1960 |
| GB | 2117249 | 10/1983 |
| JP | 2001-520087 | 10/2001 |
| JP | 2002/528676 A | 9/2002 |
| WO | WO 90/04424 | 5/1990 |
| WO | WO 92/12747 | 1/1992 |
| WO | 92/11049 A1 | 7/1992 |
| WO | WO 97/29798 | 8/1997 |
| WO | WO 98/11927 | 3/1998 |
| WO | WO 99/20330 | 4/1999 |
| WO | WO 02/096487 | 12/2002 |
| WO | WO 03/101368 | 12/2003 |
| WO | WO 2004/014476 | 2/2004 |
| WO | WO2005/002652 | 1/2005 |
| WO | WO 2007/118907 | 10/2007 |

OTHER PUBLICATIONS

English translation of CH 265347.
International Preliminary Examination Report issued in connection with commonly owned PCT Application No. PCT/DK02/00813, mailed Mar. 29, 2004.
International Search Report issued in connection with commonly owned PCT Application No. PCT/EP2007/053865, mailed Jul. 23, 2007.
International Search Report issued in connection with commonly owned PCT Application No. PCT/EP2007/053866, mailed Aug. 9, 2007.
Search Report issued in connection with commonly owned PCT Application No. PCT/DK02/00813, mailed Mar. 25, 2003.
Written Opinion issued in connection with commonly owned PCT Application No. PCT/DK02/00813, mailed Mar. 3, 2004.
Order Dismissing Appeal mailed Mar. 19, 2010 in U.S. Appl. No. 10/308,367, filed Dec. 3, 2002 by Nielsen et al.
Final Office Action mailed Oct. 10, 2008 in U.S. Appl. No. 10/308,367, filed Dec. 3, 2002 by Nielsen et al.
Advisory Action mailed Jul. 23, 2008 in U.S. Appl. No. 10/308,367, filed Dec. 3, 2002 by Nielsen et al.
Final Office Action mailed May 12, 2008 in U.S. Appl. No. 10/308,367, filed Dec. 3, 2002 by Nielsen et al.
Non-Final Office Action mailed Jan. 8, 2008 in U.S. Appl. No. 10/308,367, filed Dec. 3, 2002 by Nielsen et al.
Final Office Action mailed Aug. 6, 2007 in U.S. Appl. No. 10/308,367, filed Dec. 3, 2002 by Nielsen et al.
Non-Final Office Action mailed Apr. 27, 2007 in U.S. Appl. No. 10/308,367, filed Dec. 3, 2002 by Nielsen et al.
Final Office Action mailed Jan. 8, 2007 in U.S. Appl. No. 10/308,367, filed Dec. 3, 2002 by Nielsen et al.
Non-Final Office Action mailed Jul. 7, 2006 in U.S. Appl. No. 10/308,367, filed Dec. 3, 2002 by Nielsen et al.
Non-Final Office Action mailed Sep. 22, 2005 in U.S. Appl. No. 10/308,367, filed Dec. 3, 2002 by Nielsen et al.
Advisory Action mailed Feb, 23, 2005 in U.S. Appl. No. 10/308,367, filed Dec. 3, 2002 by Nielsen et al.
Final Office Action mailed Oct. 20, 2004 in U.S. Appl. No. 10/308,367, filed Dec. 3, 2002 by Nielsen et al.
Non-Final Office Action mailed Mar. 26, 2004 in U.S. Appl. No. 10/308,367, filed Dec. 3, 2002 by Nielsen et al.
Notice of Allowance mailed Jan. 7, 2003 in U.S. Appl. No. 09/111,832, filed Jul. 8, 1998 by Poulsen et al.
Final Office Action mailed Aug. 12, 2002 in U.S. Appl. No. 09/111,832, filed Jul. 8, 1998 by Poulsen et al.
Non-Final Office Action mailed Dec. 14, 2001 in U.S. Appl. No. 09/111,832, filed Jul. 8, 1998 by Poulsen et al.

* cited by examiner

FLUID INFUSION SYSTEM, A METHOD OF ASSEMBLING SUCH SYSTEM AND DRUG RESERVOIR FOR USE IN THE SYSTEM

CROSS-REFERENCE TO RELATED APPLICATIONS

This application is a 35 U.S.C. §371 national stage application of International Patent Application PCT/EP2007/053865 (published as WO 2007/118907), filed Apr. 19, 2007, which claimed priority of Danish Patent Application PA 2006 00540, filed Apr. 19, 2006; this application further claims priority under 35 U.S.C. §119 of U.S. Provisional Application 60/797,447, filed May 3, 2006.

The present invention relates generally to medical delivery systems for managing medical therapy. More specifically, the invention relates to a fluid infusion system comprising a medication reservoir for containing a medical fluid and for use in combination with a fluid infusion pump, wherein the medication reservoir comprises a slideable piston having means for enhancing the frictional engagement between the piston and the reservoir wall.

BACKGROUND OF THE INVENTION

In the disclosure of the present invention reference is mostly made to the treatment of diabetes by injection of insulin, however, this is only a preferred use of the present invention.

Diabetes mellitus is the common name for at least 2 different diseases, one characterised by immune system mediated specific pancreatic beta cell destruction (insulin dependent diabetes mellitus (IDDM) or type 1 diabetes), and another characterised by decreased insulin sensitivity (insulin resistance) and/or a functional defect in beta cell function (non-insulin dependent diabetes mellitus (NIDDM) or type 2 diabetes).

The principal treatment of type 1 diabetes is straight forward substitution of the missing insulin secretion, whereas treatment of type 2 is more complicated. More specifically, in early stages of type 2 diabetes treatment a number of different types of drugs can be used, e.g. drugs which increase insulin sensitivity (ciglitazones), decrease hepatic glucose output (e.g. metformin), or reduce glucose uptake from the gut (alfa glucosidase inhibitors), as well as drugs which stimulate beta cell activity (e.g. sulfonylurea/meglitinides). However, the above-described deterioration is reflected in the fact that beta cell stimulators will eventually fail to stimulate the cell, and the patient has to be treated with insulin, either as mono therapy, or in combination with oral medication in order to improve glucose control.

Currently, there are two principal modes of daily insulin therapy, the first mode including syringes and insulin injection pens. These devices are simple to use and are relatively low in cost, but they require a needle stick at each injection, typically 3-4 times or more per day. The second mode is infusion pump therapy, which entails the purchase of a portable but relatively expensive pump, for which reason the initial cost of the pump is a barrier to this type of therapy. Although more complex than syringes and pens, the pump offer the advantages of continuous infusion of insulin, precision in dosing and optionally programmable delivery profiles and user actuated bolus infusions in connections with meals. Further, in combination with a blood glucose sensor an infusion pump may provide fully automatic closed loop control of insulin infusion.

The fluent medicine is usually contained in a reservoir, which can be either a user fillable reservoir or a pre-filled disposable reservoir. Such known reservoir can be provided as a cylindrical barrel having a penetrable membrane at a proximal end and a movable piston at the opposite distal end. A conduit penetrating the membrane is mounted at the proximal end.

When the piston is moved towards the membrane, the fluent medicament contained in the reservoir is pressed out through the conduit. When the conduit is mounted it is however possible for the medicament to escape out through the conduit and for the piston to move towards the proximal end only by the influence of gravity. In delivery systems such as pump systems, where the conduit is in contact with the fluid medicament for a substantial period of time, it is normal procedure to connect the plunger to the plunger rod in order to provide a controlled forward movement of the plunger thereby preventing the reservoir from emptying itself.

Some commercially available infusions pumps are adapted to include a user-fillable reservoir, which the user fills with the medicament prior to use. Such fillable reservoirs usually includes a piston having the back wall provided with an interior thread into which a pull rod is screwed. The piston can then be moved backwards inside the fillable reservoir, and the reservoir can be filled with medicine from a vial. Once the reservoir has been filled, the pull rod is disconnected from the piston and the reservoir is inserted into the medication pump.

Depending on the specific design of the pump drive system, a linear actuation member is adapted to engage the piston when a reservoir is inserted into the medication pump. Some coupling mechanisms rely on a positive locking of the linear actuation member to the piston where the coupling is maintained throughout the use of a single reservoir.

Other pump systems may rely on a simple abutment between the linear actuation member and the piston, i.e. the linear actuation member is not positively locked to the piston during pump use. However, in order to take the abovementioned self-emptying into consideration, the friction between the piston and the reservoir wall has to be considered to avoid the risk of free-flow. In commercially available user fillable reservoirs, such as the ones designed for use in insulin pumps marketed by Medtronic Minimed under the trademark PARADIGM, the piston and reservoir are designed such that sufficient friction is established between the piston and the reservoir wall.

Generally, it is desirable to use pre-filled reservoirs in pump systems. However, various conditions have to be taken into consideration in order to provide a reservoir which is suitable for long term storage of insulin. Conventional reservoir materials such as glass for the reservoir wall and specific rubber compositions for completely or partly constituting the piston are generally accepted for constituting insulin prefilled cartridges. Usually, prior to filling, conventional glass cartridges are subject to a siliconization process in order to reduce static friction between the cartridge wall and the piston.

Due to reduced friction compared to the above mentioned user-fillable reservoirs, conventional prefilled glass cartridges cannot be readily adopted in pump systems which has a linear actuation member which solely abuts the piston, i.e. does not provide a positive lock, and which at the same time is not provided with additional means for excluding free-flow.

Various different references describe mechanisms for ensuring disconnectable but positive locking of a linear actuation member and a piston situated in a reservoir.

However, due to the specific design of the infusion pump, total freedom with respect to the movements required for coupling and uncoupling a linearly moving actuation member and a reservoir comprising a piston is seldom obtainable. These limitations both arise due to the specific movements of the linear actuation member which may comprise axial only or axial as well as rotating movements, and due to the specific movements required when inserting or removing a reservoir into the reservoir receiving section of the infusion pump.

WO patent application No. 2005/002652 discloses an infusion or injection device being provided with a mechanism which secures the connection between a piston and an output member against axial displacement. The connection is established by axially displacing the output member and the piston relative to each other. Disconnection is obtained by relatively twisting the output member with respect to the piston.

According to the various embodiments shown in WO patent application No. 2005/002652, the connection between the actuation member and the piston is provided by a number of resilient engagement parts extending from the actuation member, where the end of the engagement parts cooperates with an internal thread formed in the piston. Due to the piston being formed of a flexible material, and due to the limited contact surface between the piston thread and the engagement parts of the actuation member, a connection is established which is rather flexible in the axial direction, leading to inaccuracies in the amount of fluid dispensed by the infusion pump.

The same deficiencies applies to the connection shown in U.S. Pat. No. 6,447,487 which specifically addresses the problem of free flow. Here a rigid actuation member frictionally engages an inner thread of a rubber piston. Due to the piston being elastically deformable, the engagement between the actuation member and the piston allows for a relative high degree of flexibility along an axis parallel to the dispensing movement.

U.S. Pat. No. 6,800,071 discloses a piston for a fluid medicament reservoir where the piston is formed by a flexible sealing part and a more rigid part inserted in the flexible part, thereby providing rigidity and stability to the flexible part. As discussed in this reference, some pump systems may have an occlusion detection system which uses the axial force on the drive train as an indicator of pressure within a reservoir. The provision of having a relatively stiff and incompressible piston improves the speed that an possible occlusion can be detected. However, the flexible piston part is provided with threads for threadedly coupling the piston to corresponding threads on a linear actuation member of the pump drive system. As the piston threads are formed in the flexible material of the piston, a connection is obtained that may induce some resilience between the piston and the linear actuation member, which again lead to inaccuracies in the amount of fluid expelled from the reservoir, and, the performance of the occlusion detection system is not optimal.

U.S. Pat. No. 6,569,126 and GB patent application No. 2,117,249 discloses syringes having a slideable piston inserted into the syringe. The disclosed syringes are provided with pistons having additional means for excluding rearwards movement of the piston. Neither of those references include disclosure of piston constructions having means for a well defined enhancement of the frictional engagement between piston and syringe wall during forward movement of the piston.

In view of the above, it is an object of the present invention to provide a drug infusion system having increased safety against free flow of fluid from the reservoir. A further object of the present invention is to provide a reservoir for containing a drug to be infused into a patient, wherein the the piston of the reservoir is provided with means for ensuring enhanced control of frictional forces between the piston and the reservoir wall.

Further objects and advantages of the present invention will be apparent from the below disclosure as well as from the description of exemplary embodiments.

DISCLOSURE OF THE INVENTION

In the disclosure of the present invention, embodiments will be described which will address one or more of the above objects or which will address objects apparent from the below disclosure as well as from the description of exemplary embodiments.

Correspondingly, in a first aspect of the invention, a fluid infusion system is provided which comprises a reservoir adapted to contain the fluid and adapted for use with a pump drive system having a linear actuation member. The reservoir comprises a proximal end adapted to connect to an infusion set, an open distal end and a cylindrical reservoir wall longitudinally extending along an axis from the proximal end to the distal end. The reservoir further comprises a piston adapted to be slideably and frictionally mounted within the reservoir and forming a fluid-tight barrier inside the reservoir. The piston comprises a piston body with at least one peripheral sealing portion made of a material having a first stiffness, wherein the sealing portion is in sealing contact with the inside surface of the reservoir wall. The piston further comprises a friction enhancing member having at least one wall engaging portion at least partially made of a material having a greater stiffness than said first stiffness. The or each wall engaging portion is arranged for frictionally engaging the cylindrical wall of the reservoir so as to exert a radially outwards directed force component against the cylindrical wall.

The friction enhancing member is adapted to increase the frictional forces exerted on the reservoir wall when the piston is forced to move in a direction towards the proximal end of the reservoir. By forming the piston with such friction increasing members, the risk of experiencing free-flow from the reservoir is reduced.

The friction enhancing member may comprise a central section so that each wall engaging portion is coupled to the central section by a flexible shank portion or arm bridging the wall engaging portion with the central section. All of the wall engaging portions may be coupled together by one particular central section, or alternatively, groups of wall engaging portions may be mutually coupled by respective separate central sections. Also, the wall engaging portions may be individually held by the piston flexible material.

In some embodiments, the one or more wall engaging portions extend in a plane substantially perpendicular to the longitudinally axis of the reservoir. Alternatively, some or all of the wall engaging portions extends at an inclined angle with respect to a plane arranged perpendicular to the longitudinally axis of the reservoir.

The flexible shank portions or arms bridging the wall engaging portions may be so arranged as to force the wall engaging portion to move only in directions substantially perpendicular to the longitudinally axis when forces are exerted onto the wall engaging portion of the friction enhancing member. In this way, a system is obtained providing enhanced rigidity when unintentional forces are exerted on the piston.

This may be obtained by forming at least a part of the flexible shank portions or arms as longitudinally extending members forming an angle relative to a plane perpendicular to the longitudinal axis such as greater than 20 degrees, such as greater than 60 degrees. In some embodiments, the flexible shank portions are arranged at an angle of approximately 90 degrees with respect to a plane perpendicular to the longitudinal axis.

At least one of the wall engaging portions may be provided with an arcuate surface shaped to abut the interior wall surface of the cylindrical reservoir wall along the arcuate surface.

The piston body has a first external proximate side being adapted to contact the fluid and an external distal side defining an opening leading into a cavity. In such a piston body, the frictional enhancing member may be provided with means for fixedly retaining said frictional enhancing member inside said cavity.

The piston may further comprise a third member adapted to releasably couple to the linear actuation member of the infusion pump drive system. The third member may be adapted to fixedly secure said third member to said friction enhancing member and/or said piston body. The linear actuation member may comprise one or more protrusions, such as a circular rim or one or more threaded portions so that the third member may engage said one or more protrusions.

In some embodiments, the friction enhancing members are partly or fully made of steel or spring steel. Alternatively, the friction enhancing members may be made of a hard resin material. Further, in some embodiments the piston body and the at least one sealing portion of the piston are formed unitarily.

The piston body may comprise a material having a greater stiffness than the material of the at least one sealing portion of the piston, and in such systems, the piston body and the friction enhancing member may be formed unitarily.

In alternative embodiments the piston is formed by co-molding the piston body and the friction enhancing member so that the friction enhancing member is partly or fully encapsulated by the piston body.

In a further aspect a method is provided for assembling a fluid infusion system suitable for infusing a medication fluid, the method comprising the steps of:

(a): providing a fluid infusion pump comprising a drive system having a linear actuation member;

(b): providing a reservoir adapted to contain the fluid, the reservoir comprising a proximal end adapted to connect to an infusion set, an open distal end, a cylindrical reservoir wall longitudinally extending along an axis from the proximal end to the distal end, and a piston adapted to be slideably and frictionally mounted within the reservoir and forming a fluid-tight barrier inside the reservoir, wherein the piston comprises a piston body with at least one peripheral sealing portion sealingly in contact with the inside surface of the reservoir wall, the sealing portion made of a material having a first stiffness, and wherein the piston further comprises a friction enhancing member having one or more wall engaging portions, wherein the or each wall engaging portion is at least partially made of a material having a greater stiffness than said first stiffness, the or each wall engaging portion frictionally engaging the cylindrical wall of the reservoir and being arranged to exert a radially outwards directed force component against the cylindrical wall; and (c): coupling the reservoir to the infusion pump.

In a yet further aspect a reservoir for use in the above described fluid infusion system is provided.

The reservoir of all the above described aspects may be formed by a section of glass forming the cylindrical wall. Said wall may on its internal surface be subjected to a siliconizing process. The reservoir may form a pre-filled cartridge with the medicament accommodated therein for forming a unit ready to be used in an infusion pump.

As used herein, the terms "drug", "medicament" or "fluid" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the terms "subcutaneous" and "transcutaneous" infusion is meant to encompass any method of transcutaneous delivery to a subject.

BRIEF DESCRIPTION OF THE DRAWINGS

In the following, the invention will be further described with references to the drawings, wherein.

DESCRIPTION OF EXEMPLARY EMBODIMENTS

Figure 1:
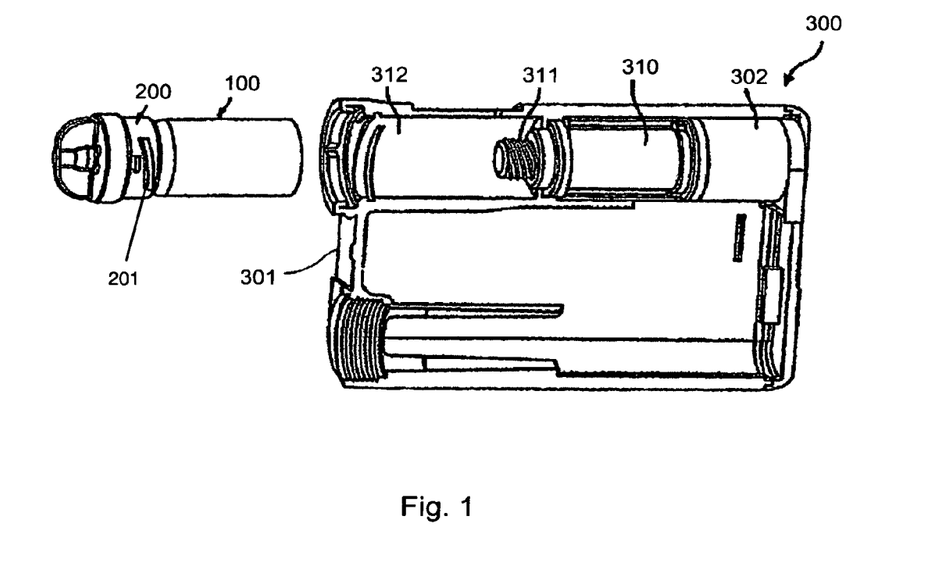
FIG. 1 is a cut-away perspective view of a conventional infusion pump designed for use with the reservoir according to the present invention.

FIG. 1 is a schematic representation of an exemplary infusion pump 300 adapted for receiving a medicament containing reservoir 100 in accordance with the present invention. This schematic representation corresponds to the infusion pump disclosed in U.S. Pat. No. 6,800,071 which is hereby incorporated in its entirety. Infusion pump 300 includes reservoir receiving cavity 312 adapted to accommodate a user-filled or pre-filled insulin reservoir 100.

Reservoir 100 is provided with coupling means for releasably securing a connector 200 to reservoir 100. Connector 200 further forms part of an infusion set which includes an infusion set tubing (not shown). Also, connector 200 comprises coupling means 201 for coupling with the housing part 301 of the infusion pump 300, whereby both infusion tubing and the reservoir are coupled to the housing 301 of the infusion pump 300 when connector 200 is secured to the pump housing.

FIG. 1 also schematically depicts a piston drive system comprising a driving device such as a motor 302 arranged for driving a linear actuation member 310 for successively driving a piston accommodated in the reservoir 100 towards the proximal end of the reservoir. In some embodiments of this invention, the linear actuation member 310 is provided with protrusions in the form of an external thread 311, which is adapted for coupling to the piston included in reservoir 100. In other embodiments, the linear actuation member 310 simply abuts the piston. The remaining parts of the infusion pump are not shown or described here, but are considered the object of a normal design procedure performed by the skilled person along the lines set out in the present specification and in the prior art.

The reservoir 100 according to a first embodiment of the invention includes a proximal end closed by a piercable membrane (not shown) and means adapted to connect to an infusion set, an open distal end and a cylindrical wall longitudinally extending between the proximal and the distal end of the reservoir.

Figure 2:
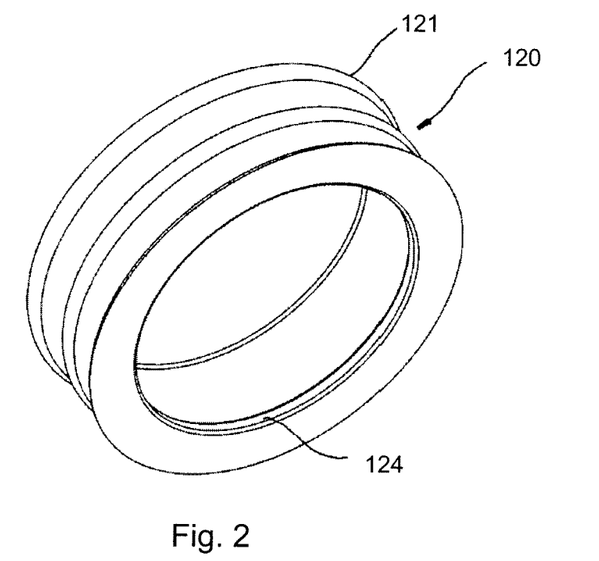
FIG. 2 shows a perspective view of a piston body according to the present invention.

In accordance with the present invention, FIG. 2 shows a piston body 120 comprising one or more circumferential sealing portions 121 for providing a fluid-tight seal against the reservoir wall. At least the sealing portions 121 of piston body 120 are formed by an elastomeric material such as rubber defining a first stiffness. The rear part of piston body 120 includes a cavity which is adapted to receive a friction enhancing member 110 (see FIG. 3), and a linear actuation member 310 of an infusion pump 300.

Figure 3:
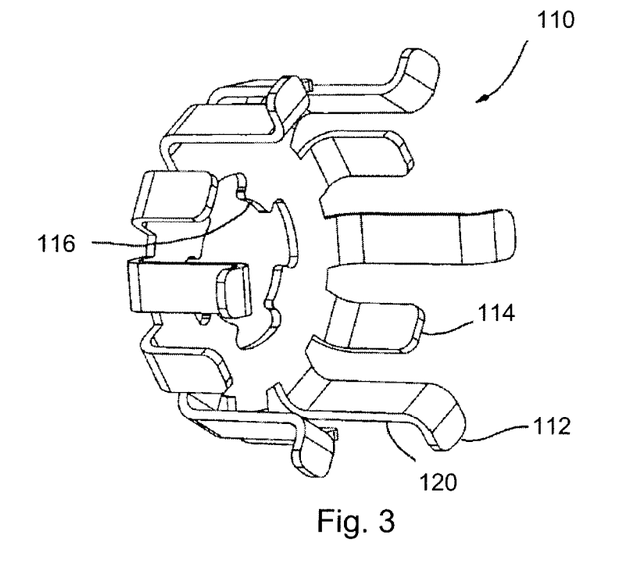
FIG. 3 shows a perspective view of a friction enhancing member according to the invention.

At the distal end the cavity adjacent the opening in piston body 120, a circular inwardly extending rim 124 is provided which is adapted to mate with retaining means 114 of the friction enhancing member 110. Further, as shown in FIG. 3, the friction enhancing member 110 is provided with a number of longitudinally extending flexible shanks or arms which forms connections towards radially extending friction engaging endpoints 112 adapted to frictionally engage the reservoir wall 101.

In accordance with the invention, the friction enhancing member 110 is at least partially made of a material of greater stiffness than the material forming the sealing portion 121 of the piston body 120. However, the material of the friction enhancing member are selected and the dimensioning of this member is chosen so as to provide a flexible component. The material partly or fully constituting the friction enhancing member may be selected as a steel material, a spring steel, a composite material or a plastic material.

Friction enhancing member 110 generally has a disc or dish-shaped central wall section 115 extending in a plane generally perpendicular to the longitudinal axis of the reservoir. The friction enhancing member 110 is so dimensioned that it exerts a force against opposing surfaces of the piston body cavity so that the friction enhancing member 110 is fixedly retained with respect to the piston body 120. The distal face of wall section 115 is adapted to receive the end face of a linear actuation member 310 so that the linear actuation member 310 can be seated in abutment with the friction enhancing member 110.

Although not shown, when the piston body 120 is made of an elastomeric material, the dish-shaped wall section may be formed generally convex in order to stretch the inner proximate end face of the piston body 120, when friction enhancing member 110 is inserted therein.

This provision tends to minimize the flexing of the piston body 120 if a reduced liquid pressure occurs inside the reservoir, i.e. if the infusion pump is positioned above the needle of an infusion set which is attached to the infusion pump.

In general, the piston body 120 and the friction enhancing member 110 are so designed that complete uninterrupted contact is maintained between these two elements during all possible operating conditions.

Figure 4:
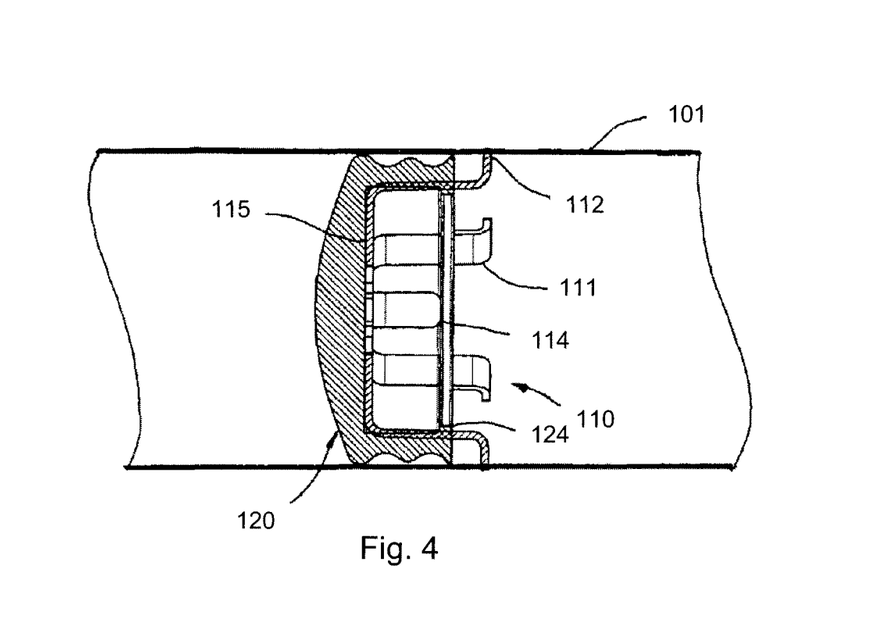
FIG. 4 is a sectional plan view of the piston body and friction enhancing member shown in FIGS. 2 and 3 inserted into a reservoir.

A section of the reservoir 100 is shown in FIG. 4, where 101 denotes the reservoir wall. Also shown in FIG. 4 is a piston assembly formed by the piston body 120 and friction enhancing member 110. The figure shows the elements superposed in their unstressed condition and indicates that the proximate wall section of the piston body 120 will be stretched when friction enhancing member 110 is inserted into the cavity formed in the piston body 120. Also the side section of the piston body 120 will be stressed or expanded in an axial direction by the retaining means 114 of friction enhancing member 110.

The piston assembly is slideably mounted along the longitudinal axis from the distal end of the reservoir towards the proximal end in order to expel medication from the proximal end of the reservoir.

Prior to insertion of piston assembly (110, 120) into the cylindrical wall section 101 of the reservoir, the piston body 120 is in a generally unstressed condition, allowing friction enhancing member 110 to be inserted into the cavity formed in piston body 120. After the piston assembly has been inserted into the cylindrical wall section 101 of the reservoir, the piston body 120 is radially compressed by the wall sections 101 of the reservoir thereby providing a fixed retainment of friction enhancing member 110 inside piston body 120. Due to the form-fitting engagement of friction enhancing member 110 and the piston body 120, and due to the large contact surface between these two elements, a relatively stiff connection is obtained providing minimal flexibility in the longitudinal direction.

When the piston assembly is inserted into the reservoir, the protruding arms 111 ending in friction engaging endpoints 112 are compressed radially inwards due to a reduced diameter of the inner wall of the reservoir compared to the effective diameter of the protruding arms in their unstressed condition. Due to the elastically deformable material of friction enhancing member 110 and due to the said radial compression, the friction enhancing member 110 exerts a force on the cylindrical wall 101, whereby this force has a radially outward directed force component. A suitable force in the order of 200 Mpa may be exerted on the side wall of the reservoir. Due to an increase in the frictional engagement between friction engaging portion 112 and the reservoir wall 101, the piston is frictionally held abutted against the linear actuation member 310.

The wall engaging portions 112 of friction enhancing member 110 may extend in a plane perpendicular to the longitudinal axis of the reservoir. Alternatively, each of the wall engaging portions 112 may be slightly inclined to extend radially outwards and in a direction against the distal end of the reservoir so as to facilitate insertion of friction enhancing member 110 into the reservoir.

Depending on the material of the wall engaging portions 112 and the material chosen for the reservoir wall, the wall engaging portions 112 may be polished or alternatively be provided with a coating.

In a second embodiment of the invention, a third member 130 (shown in FIG. 5) is introduced into the piston assembly according to the first embodiment described above. The third member 130 provides coupling engagement between the piston body 120 or the friction enhancing member 110 and the linear actuation member 310. Also, the third member 130 provides additional stability to the piston.

Figure 5:
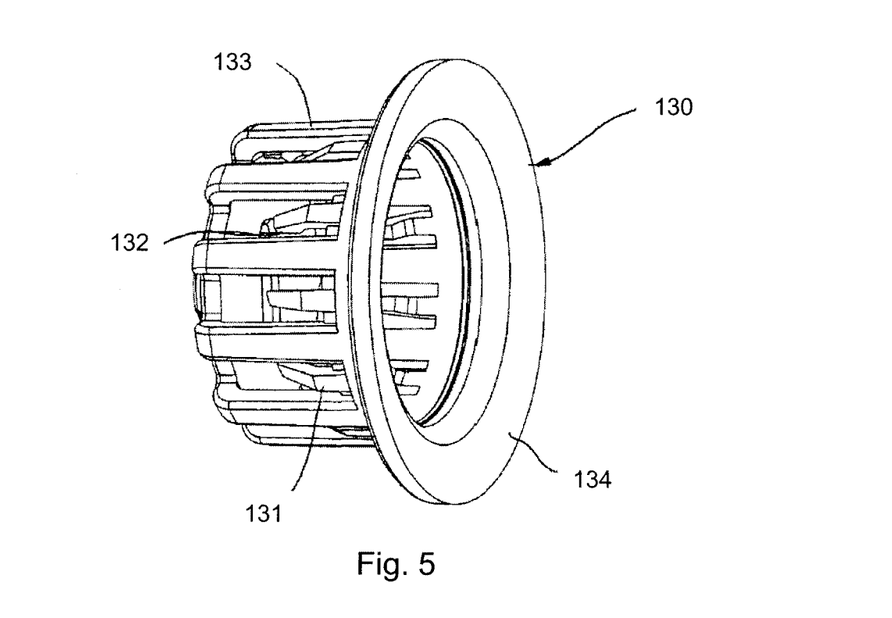
FIG. 5 shows a perspective view of an engagement member for coupling to a linear actuator according to a second aspect of the invention.

The third member 130 may be provided with coupling means (not shown) adapted for keyed connection to mating key-shaped coupling means 116 formed in friction enhancing member 110 (shown in FIG. 3).

The third member 130 comprises a generally dish- or disc-shaped proximal wall section being adapted to be seated against the end face of linear actuation member 310. The third member 130 further comprises one or more longitudinally extending members 133 connecting said proximal wall section to circular rim 134 arranged at the distal side of the third member 130. From circular rim 134, one or more connective members 131 generally extends in the longitudinal direction of the reservoir, thereby being substantially rigid in the longitudinal direction. Due to the shape of the connective members 131 and the material chosen, the connective members are able to flex in the radial direction. The connective members 131 are adapted to couple with the linear actuation member 310 of an infusion pump, when linear actuation member 310 is inserted into the piston assembly (110, 120, 130).

Although the connective members 131 are shown as extending from circular rim 134, other alternative embodiments may include connective members 131 extending from the proximal wall section of the third member 130. Still, other alternatives may include connective members 131 which may be connected both to circular rim 134 and the proximal wall section of the third member 130.

Figure 6:
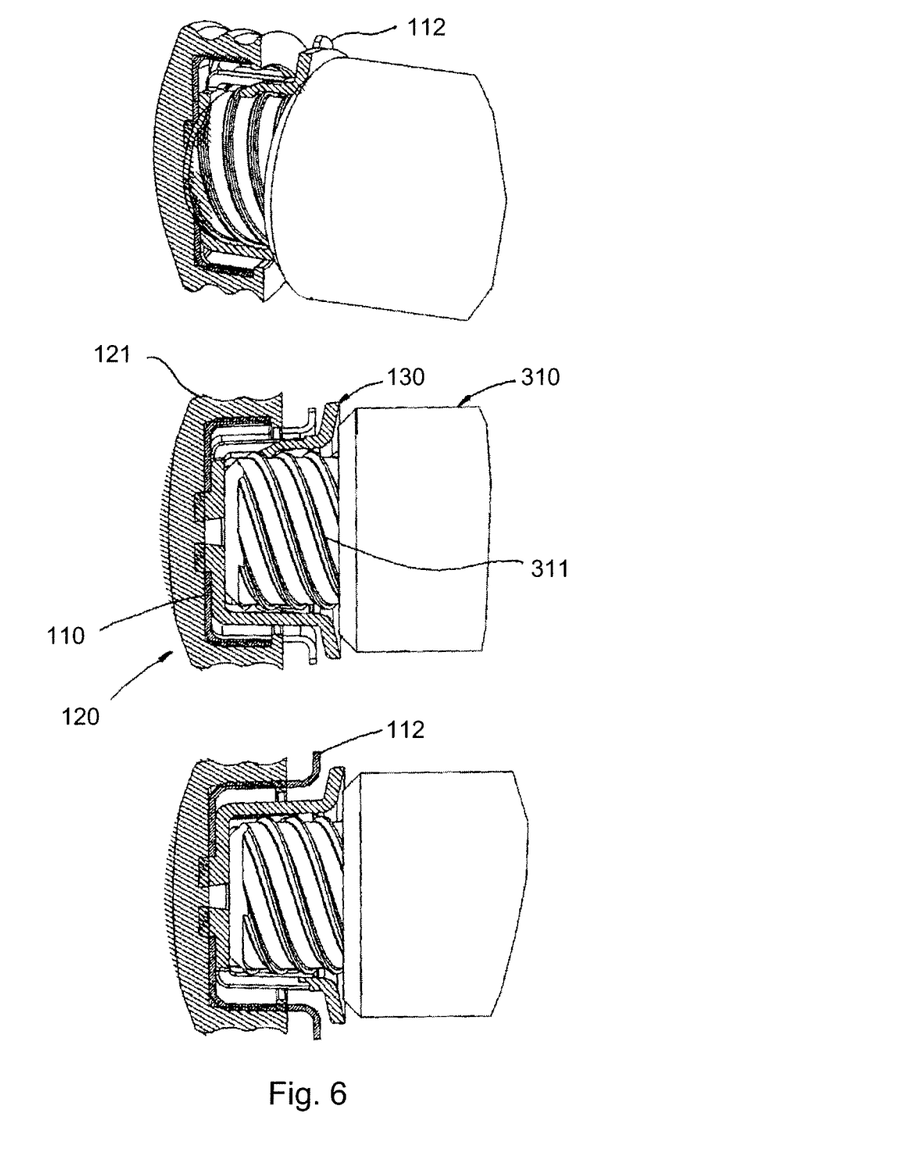
FIG. 6 shows cut-away perspective views of the piston assembly of the second embodiment coupled to a linear actuation member.

In the second embodiment shown in FIG. 6, connective members 131 are formed as a number of arms extending in the proximal direction, where each arm is provided with a protrusion 132 which are adapted to mate with protrusions formed on linear actuation member 310, i.e. to snap or catch behind protrusions formed on linear actuation member 310.

If the protrusions 311 of linear actuation member 310 are formed as a thread, the connective members 131 may be provided with protrusions 132 arranged in a common plane perpendicular to the longitudinal axis of the reservoir. Further, to ensure line contact between threads of linear actuation member 310 and the protrusions 132, the protrusions 132 may be formed with inclined surfaces (not shown) corresponding to the pitch of the thread of the linear actuation member 310.

If the protrusions of linear actuation member 310 are formed as one or more circumferential ridges, each of the protrusions 132 may be positioned in mutual different distances from the dish-shaped wall section. In this way, it is ensured that at least some of the protrusions 132 catches behind one ridge formed on linear actuation member 310, thereby ensuring a rigid connection having no play.

The number of connective members 131 is generally chosen on the basis of the particular design of the linear actuation member 310 so that at least one connective member is able to engage corresponding protruding elements of the linear actuation member 310. When the protrusions of the linear actuation member 310 forms a thread 311, the number of connective members 131 preferably is in the order of 10-15. Thereby it is ensured that at least one protrusion 132 engages a groove between two consecutive threads 311.

Further, a pure frictional engagement may be obtained. Particularly, this is the case if the linear actuation member 310 is not provided with protrusions. In this case, the connective members 131 are formed to exert a radially inward directed force on linear actuation member 310, the force exerted by the connective members being adapted to grip firmly on the linear actuation member 310.

The third member 130 is preferably formed with a channel or opening extending from the distal side to the proximate side of the third member. Thereby it is ensured that the piston assembly can be properly auto-claved. Also, the piston body 120 and the friction enhancing member 110, and the third member 130, if included, are formed so that, during auto-claving, several piston assemblies arranged in a stacked formation cannot stick together and draw vacuum. This can be obtained by ensuring that the friction enhancing member 110 or the third member 130 are dimensioned to obstruct the adherence between two consecutive piston assemblies.

According to the second embodiment, FIG. 6 shows perspective cut-away views of the piston body 120, the friction enhancing member 110 and the third member 130. Furthermore FIG. 6 shows a linear actuation member 310. The four elements depicted are shown superposed in their relaxed state as they appear when not mutually connected. Again, it is readily apparent that the piston body is expanded by the insertion of the friction enhancing member 110 into the piston body 120. Thereby a relatively rigid piston can be obtained.

In the embodiments shown, the connection between the piston assembly and the linear actuation member 310 may be established as a pure linear axial displacement. However, the connection can also be established where one of the two elements are rotated with respect to the other.

The disconnection between the piston assembly and the linear actuation member 310 may occur by a purely linear axial displacement without jamming the connective elements. Preferably, the connection may be designed to permit disengagement by exerting a linear disengagement force of greater than 1N and less than 10 N. Also, the disconnection may be provided by a relative twisting of the two elements.

In the above described embodiments, the piston body 120, the friction enhancing member 110 and the third member 130, if included, are provided as distinct members being assembled before insertion of the piston assembly into the reservoir. Alternatively, the friction enhancing member 110 may be fully or partly molded into the piston body 120 by an injection molding operation, whereby a relatively less stiff material forming the piston member 120 may be designed to fill out the intervening space between the protruding arms 111 of friction enhancing member 110.

In a further embodiment, the protruding arms 111 of the friction enhancing member 110 may be radially inwardly compressed during a molding operation, where the material forming the piston body or the piston seal are injection molded partly or fully encircling the protruding arms 111.

The materials chosen for the reservoir wall can be glass or a material made from a cyclic olefin copolymer (COC), or alternatively, polypropylene. The materials for the piston body sealing portion 121 may be any elastomeric material suitable for making a fluid-tight sealing while being compatible for long time storage of the medicament contained in the reservoir. The materials chosen for the friction enhancing member may be selected as a steel material, a spring steel, a composite material or a plastic material. The materials chosen for the third member may fully or at least partially include metal, plastic, COC or polypropylene. If a plastic material is used, the stiffness of the material should be so that the connective members are substantially stiff in the longitudinal direction while being able to flex in the radial direction. Also, in some embodiments, the connective members may be formed partly of metal.

In the above described second embodiment, the linear actuation member 310 is formed as a rod for engaging a cavity in the piston assembly (110, 120, 130). Alternatively, the linear actuation member 310 may be formed with a cavity where connective members 131 extending from third member 130 are adapted to be inserted into the cavity of the linear actuation member 310 to provide an engagement interface.

Even though the above described embodiments comprises a piston body creating a fluid tight barrier, the piston assembly according to the invention may be formed as a relatively rigid core member in fluid contact with the fluid to be contained inside the reservoir, and wherein the sealing portion are formed as a circumferential seal arranged in a circular channel formed in the circumferential wall of the core member. In this arrangement, the seal may be provided as an o-ring. Also, several distinct sealing members may be arranged at axially different portions of core member. In those further embodiments the fluid-tight seal of the piston assembly is obtained by the core member as well as the one or more peripheral seals.

When the piston body is made of a material different than the peripheral seals, the piston body may be formed unitarily with the friction enhancing member.

While the above embodiments are based on reservoirs having a cylindrical wall, the invention may just as well apply to reservoirs having polygonal shaped cross section, such as triangular or rectangular shaped cartridges. The reference to circular or radial measures may be adapted to these polygonal shaped embodiments as well, without departing from the scope of the present invention.

In the above description of the exemplary embodiments, the different structures providing the desired relations between the different components just as the means providing the described functionality for the different components of a suitable infusion pump for use in connection with the inventive reservoir have been described to a degree to which the concept of the present invention will be apparent to the skilled reader. The detailed construction and specification for the different structures are considered the object of a normal design procedure performed by the skilled person along the lines set out in the present specification.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. A fluid infusion system for infusing a medication fluid comprising:
    a reservoir adapted to contain the fluid and adapted for use with a pump drive system having a linear actuation member, the reservoir comprising:
    a proximal end adapted to connect to an infusion set;
    an open distal end;
    a cylindrical reservoir wall that extends along a longitudinal axis from the proximal end to the distal end; and
    a piston adapted to be slideably and frictionally mounted within the reservoir and forming a fluid-tight bather inside the reservoir; the piston comprising a piston body with at least one peripheral sealing portion made of a material having a first stiffness, said at least one sealing portion in sealing contact with the inside surface of the reservoir wall,
wherein the piston further comprises a friction enhancing member adapted to be coupled to the piston, the friction enhancing member comprising a central section and one or more wall engaging portions coupled to the central section by a respective flexible shank portion bridging the one or more wall engaging portions with the central section, wherein the one or more wall engaging portions are at least partially made of a material having a greater stiffness than said first stiffness, the one or more wall engaging portions frictionally engaging the cylindrical wall of the reservoir and being arranged to exert a radially outwards directed force component against the cylindrical wall, and wherein the respective flexible shank portion(s) is/are so configured that the respective wall engaging portions(s) is/are movable relative to the central section only in directions substantially perpendicular to said longitudinal axis.

2. The fluid infusion system as defined in claim 1, wherein at least a part of each of the respective flexible shank portions are formed as longitudinally extending members forming an angle greater than 20 degrees relative to a plane perpendicular to said longitudinal axis.

3. The fluid infusion system as defined in claim 1, wherein at least one of the one or more wall engaging portions extends in a plane generally perpendicular to the longitudinal axis of the reservoir.

4. The fluid infusion system as defined in claim 1, wherein at least one of the one or more wall engaging portions extends at an inclined angle with respect to a plane arranged perpendicular to the longitudinal axis of the reservoir.

5. The fluid infusion system as defined in claim 1, wherein at least one of the one or more wall engaging portions is provided with an arcuate surface shaped to abut the interior wall surface of the cylindrical reservoir wall along the arcuate surface.

6. The fluid infusion system as defined in claim 1, wherein the piston body has a first external proximate side being adapted to contact the fluid and an external distal side defining an opening leading into a cavity, and said frictional enhancing member is fixedly retained inside said cavity.

7. The fluid infusion system as defined in claim 6, wherein said piston further comprises a third member adapted to releasably couple to said linear actuation member and adapted to fixedly secure said third member to at least one of said friction enhancing member and said piston body.

8. The fluid infusion system as defined in claim 7, wherein said linear actuation member comprises one or more protrusions and the third member is adapted to engage said one or more protrusions.

9. The fluid infusion system as defined in claim 1, wherein said friction enhancing member is at least partly made of steel or spring steel.

10. The fluid infusion system as defined in claim 1, wherein the piston body and the at least one sealing portion are formed unitarily.

11. The fluid infusion system as defined in claim 1, wherein the piston body is made of a material having a greater stiffness than the material of the at least one sealing portion, and the piston body and the friction enhancing member are formed unitarily.

12. The fluid infusion system as defined in claim 1, wherein the piston is formed by co-molding said piston body and said friction enhancing member so that said friction enhancing member is partly encapsulated by the piston body.

13. A method for assembling a fluid infusion system suitable for infusing a medication fluid, the method comprising:
    providing a fluid infusion pump comprising a drive system having a linear actuation member;
    providing a reservoir adapted to contain the fluid, the reservoir comprising:
        a proximal end adapted to connect to an infusion set;
        an open distal end;
        a cylindrical reservoir wall that extends along a longitudinal axis from the proximal end to the distal end; and a piston adapted to be slideably and frictionally mounted within the reservoir and forming a fluid-tight bather inside the reservoir; the piston comprising a piston body with at least one peripheral sealing portion made of a material having a first stiffness, said at least one sealing portion in sealing contact with the inside surface of the reservoir wall, wherein the piston further comprises a friction enhancing member adapted to be coupled to the piston, the friction enhancing member comprising a central section and one or more wall engaging portions coupled to the central section by a respective flexible shank portion bridging the one or more wall engaging portion with the central section, wherein the wall engaging portion(s) is/are at least partially made of a material having a greater stiffness than said first stiffness, at least one wall engaging portion frictionally engaging the cylindrical wall of the reservoir and being arranged to exert a radially outwards directed force component against the cylindrical wall and wherein the respective shank portion(s) is/are so configured that the respective wall engaging portion(s) is/are movable relative to the central section only in directions substantially perpendicular to said longitudinal axis; and coupling the reservoir to the infusion pump.

14. A reservoir for use in the fluid infusion system according to claim 1, the reservoir adapted to contain a fluid for infusion into the body of a patient and adapted for use with a drive system having a linear actuation member, the reservoir comprising:

a proximal end adapted to connect to an infusion set;
an open distal end;
a cylindrical reservoir wall that extends along a longitudinal axis from the proximal end to the distal end; and
a piston adapted to be slideably and frictionally mounted within the reservoir and forming a fluid-tight bather inside the reservoir; the piston comprising a piston body with at least one peripheral sealing portion made of a material having a first stiffness, said at least one sealing portion in sealing contact with the inside surface of the reservoir wall,
wherein the piston further comprises a friction enhancing member comprising a central section and one or more wall engaging portions coupled to the central section by a respective flexible shank portion bridging the one or more wall engaging portion with the central section, wherein the one or more wall engaging portions are at least partially made of a material having a greater stiffness than said first stiffness, the one or more wall engaging portions frictionally engaging the cylindrical wall of the reservoir and being arranged to exert a radially outwards directed force component against the cylindrical wall, and wherein at least one of the respective flexible shank portion(s) is/are so configured that the respective wall engaging portion(s) is/are movable relative to the central section only in directions substantially perpendicular to said longitudinal axis.

15. A fluid infusion system for infusing a medication fluid, the fluid infusion system comprising:

a fluid reservoir having a cylindrical wall that extends along a longitudinal axis defining an inside and outside surface;
a piston adapted to be slideably and frictionally mounted within the reservoir and forming a fluid-tight bather inside the reservoir; the piston comprising a piston body with at least one sealing portion made of a material having a first stiffness, the sealing portion being in sealing contact with the inside surface of the fluid reservoir;
a friction enhancing member that is independent of the sealing portion and is configured to mate with the sealing portion, and comprises at least one wall engaging portion coupled to the central section by a respective flexible shank portion bridging the one or more wall engaging portions with the central section, that is at least partially made of a material having a greater stiffness than the first stiffness of the sealing portion, wherein the at least one wall engaging portion frictionally engages the inside surface of the fluid reservoir and exerts a force component in a radially outward direction against the inside surface of the fluid reservoir; and
a linear actuation member operatively associated with the friction enhancing member, and wherein at least one of the respective flexible shank portion(s) is/are so configured that the respective wall engaging portion(s) is/are movable relative to the central section only in directions substantially perpendicular to said longitudinal axis.

16. A reservoir as defined in claim 14, wherein at least a part of each of the respective flexible shank portions are formed as longitudinally extending members forming an angle greater than 20 degrees relative to a plane perpendicular to the longitudinal axis.

* * * * *

UNITED STATES PATENT AND TRADEMARK OFFICE
CERTIFICATE OF CORRECTION

| | | |
|---|---|---|
| PATENT NO. | : 8,551,045 B2 | Page 1 of 1 |
| APPLICATION NO. | : 12/297340 | |
| DATED | : October 8, 2013 | |
| INVENTOR(S) | : Gunnar M. Sie et al. | |

It is certified that error appears in the above-identified patent and that said Letters Patent is hereby corrected as shown below:

In the Claims:

At column 11, claim number 1, line number 55, please replace "fluid-tight bather" with "fluid-tight barrier."

At column 13, claim number 13, line number 2, please replace "fluid-light bather" with "fluid-tight barrier."

At column 13, claim number 14, line number 36, please replace "fluid-tight bather" with "fluid-tight barrier."

Signed and Sealed this
Eleventh Day of November, 2014

Michelle K. Lee
*Deputy Director of the United States Patent and Trademark Office*